(12) United States Patent
Ouriel et al.

(10) Patent No.: US 6,749,619 B2
(45) Date of Patent: Jun. 15, 2004

(54) APPARATUS AND METHOD FOR ELIMINATING DISLODGED THROMBUS

(75) Inventors: Kenneth Ouriel, Pepper Pike, OH (US); Harry B. Goodson, Cleveland, OH (US); Roy K. Greenberg, Bratenahl, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 28 days.

(21) Appl. No.: 09/989,813

(22) Filed: Nov. 20, 2001

(65) Prior Publication Data

US 2003/0097094 A1 May 22, 2003

(51) Int. Cl.⁷ .................. A61M 29/00; A61M 31/00
(52) U.S. Cl. .................. 606/200; 604/509; 604/104
(58) Field of Search .............. 604/96.01, 104, 604/107, 105, 106, 108

(56) References Cited

U.S. PATENT DOCUMENTS

| | | | |
|---|---|---|---|
| 4,425,908 A | 1/1984 | Simon | |
| 4,706,671 A | 11/1987 | Weinrib | |
| 4,969,891 A | 11/1990 | Gewertz | |
| 5,011,488 A | 4/1991 | Ginsburg | |
| 5,021,044 A | 6/1991 | Sharkawy | |
| 5,370,609 A | 12/1994 | Drasler et al. | |
| 5,370,653 A | 12/1994 | Cragg | |
| 5,380,307 A | 1/1995 | Chee et al. | |
| 5,681,274 A | 10/1997 | Perkins et al. | |
| 5,713,853 A | 2/1998 | Clark et al. | |
| 5,800,408 A | 9/1998 | Strauss et al. | |
| 5,895,398 A | 4/1999 | Wensel et al. | |
| 5,925,016 A | 7/1999 | Chornenky et al. | |
| 5,947,985 A | 9/1999 | Imran | |
| 5,957,901 A * | 9/1999 | Mottola et al. | 604/264 |
| 5,972,019 A * | 10/1999 | Engelson et al. | 606/200 |
| 6,063,069 A * | 5/2000 | Cragg et al. | 604/508 |
| 6,066,149 A | 5/2000 | Samson et al. | |
| 6,066,158 A | 5/2000 | Engelson et al. | |
| 6,068,645 A | 5/2000 | Tu | |
| 6,080,170 A | 6/2000 | Nash et al. | |
| 6,096,001 A | 8/2000 | Drasler et al. | |
| 6,113,576 A | 9/2000 | Dance et al. | |
| 6,117,125 A | 9/2000 | Rothbarth et al. | |
| 6,129,697 A | 10/2000 | Drasler et al. | |
| 6,135,991 A | 10/2000 | Muni et al. | |
| 6,146,404 A | 11/2000 | Kim et al. | |
| 6,165,199 A | 12/2000 | Barbut | |
| 6,168,579 B1 | 1/2001 | Tsugita | |
| 6,179,813 B1 | 1/2001 | Ballow et al. | |
| 6,179,816 B1 | 1/2001 | Mottola et al. | |
| 6,245,089 B1 | 6/2001 | Daniel et al. | |
| 6,277,138 B1 | 8/2001 | Levinson et al. | |
| 6,454,775 B1 * | 9/2002 | Demarais et al. | 606/128 |

OTHER PUBLICATIONS http://www.microvena.com/MVC–NEWS.html (1 page), dated Mar. 28, 2001.
http://www.microvena.com/atd/prodoverview.html (1 pg.), dated Mar. 28, 2001.
http://www.microvena.com/atd/productimages.htm (1 pg.), dated Mar. 28, 2001.
http://www.microvena.com/atd/orderinfo.html (1 pg.), dated Mar. 28, 2001.
http://www.microvena.com/atd/atdbib.html (2 pgs.), dated Mar. 28, 2001.

(List continued on next page.)

*Primary Examiner*—Brian L. Casler
*Assistant Examiner*—Lina R Kontos
(74) *Attorney, Agent, or Firm*—Tarolli, Sundheim, Covell & Tummino L.L.P.

(57) ABSTRACT

An apparatus (10) for eliminating dislodged thrombus (78) in a blood vessel (12) comprises a catheter (72) having a plurality of infusion ports (90) and a filter (76) attached to the catheter for trapping the dislodged thrombus carried by blood flow in the blood vessel. The infusion ports (90) are disposed within the filter (76) and are operable to deliver a thrombolytic fluid to dissolve the dislodged thrombus (78) trapped in the filter (76).

11 Claims, 8 Drawing Sheets

OTHER PUBLICATIONS http://www.microvena.com/atd/casestudies/1thrombdgraft.html, (2 pgs.), dated Mar. 28, 2001.

http://www.microvena.com/atd/casestudies/6dgraft-throm.html, (2 pgs.), dated Mar. 28, 2001.

Introducing the Thrombex PMT™ System, *Edwards Lifesciences* dated 2000 (4 pgs.).

The Fogarty® Adherent Clot Catheter, *Edwards Lifesciences* dated 1996 (2 pgs.).

Castaneda Over-the-Wire™ Mechanical Brush, *Micro Therapeutics, Inc.*, dated 2000 (2 pgs.).

ProStream® Multiple Sidehole Infusion Wire, *Micro Therapeutics, Inc.*, dated 2000 (2 pgs.).

Cragg-McNamara® Valved Infusion Catheter, *Micro Therapeutics, Inc.*, dated 2000 (2 pgs.).

AngioJet® Coronary, Rapid, Decisive Thrombus Removal, *Possis Medical, Inc.*, dated 1999 (11 pgs.).

Infusion Systems, *AngioDynamics®, Inc.*, dated 2000 (6 pgs.).

* cited by examiner

APPARATUS AND METHOD FOR ELIMINATING DISLODGED THROMBUS

TECHNICAL FIELD

The present invention relates to an apparatus and method for eliminating dislodged thrombus in a blood vessel.

BACKGROUND OF THE INVENTION

Removal of thrombus from human vasculature may be accomplished via a traditional open surgical procedures, or via endovascular procedures. While open surgical procedures remain the standard for many cases, endovascular procedures are typically less invasive and often decrease the time between diagnosis and treatment. This is especially critical, for example, in lysis of a cerebrovascular clot for treatment of an acute stroke.

Current endovascular techniques for removing thrombus include mechanical and chemical approaches. Known mechanical approaches include perturbation of the thrombus via physical scraping, the application of a pressure gradient, and electromechanical stimulation. Known chemical approaches include intravenous (or systemic) delivery of a thrombolytic agent and selective delivery of a thrombolytic agent through an infusion catheter. It can be advantageous with both mechanical and chemical approaches to use a filter device to trap thrombus dislodged during the endovascular procedure and thereby prevent the dislodged thrombus from traveling downstream in the vasculature.

One of the challenges faced by surgeons using endovascular techniques to remove thrombus is the wide variation in size (axial length) of the thrombotic material. Thrombotic material in vasculature frequently ranges from 5 cm to 30 cm in axial length, requiring the surgeon to select an infusion catheter having the proper infusion length. Sometimes this selection process may occur prior to surgery, but other times the selection of the infusion catheter occurs during surgery, which requires an assortment of infusion catheters having various infusion lengths to be brought into surgery. Hence, a need exists for an infusion catheter in which the infusion length can be varied according to the size of the thrombus.

Another challenge faced by surgeons using endovascular techniques to remove thrombus arises when dislodged thrombus is trapped in a filter. The filter is typically inserted into the vasculature through a relatively small catheter. Often, the dislodged thrombus includes relatively large sections which make it difficult to retract a filter filled with such large sections of thrombus. Hence, a need exists for a thrombolysis apparatus which sufficiently reduces or, ideally, completely dissolves the thrombus trapped by the filter so that the filter can be easily retracted and removed.

SUMMARY OF THE INVENTION

The present invention is an apparatus for eliminating dislodged thrombus in a blood vessel. The apparatus comprises a catheter having a plurality of infusion ports and a filter attached to the catheter for trapping dislodged thrombus carried by blood flow in a blood vessel. The plurality of infusion ports are disposed within the filter and are operable to deliver a thrombolytic fluid to dissolve the dislodged thrombus trapped in the filter.

In accordance with another aspect, the present invention is an apparatus for eliminating dislodged thrombus in a blood vessel. The apparatus comprises relatively movable first and second tubular members. The first tubular member is partially disposed coaxially within the second tubular member. The first tubular member includes a plurality of infusion ports for delivering a thrombolytic fluid. A filter member is attached to the first and second tubular members. The filter member is radially expandable by relative movement between the first and second tubular members to stretch across the blood vessel and trap dislodged thrombus carried by blood flowing through the blood vessel. The plurality of infusion ports are located within the filter member and oriented to direct the thrombolytic fluid against the dislodged thrombus trapped in the filter member and thereby dissolve the dislodged thrombus.

According to another aspect of the present invention, a method for eliminating thrombus attached to a wall of a blood vessel is provided. According to the inventive method, a radially expandable filter assembly is inserted into the blood vessel downstream from the thrombus. The filter assembly includes a filter basket having a plurality of infusion ports disposed within the filter basket. The filter assembly is radially expanded to extend across the blood vessel. The thrombus is dislodged from the wall of the blood vessel. The dislodged thrombus is then trapped in the filter basket A thrombolytic agent in infused through the filter assembly and directed, through the plurality of infusion ports, into the filter basket to dissolve the thrombus trapped in the filter basket.

BRIEF DESCRIPTION OF THE DRAWINGS

The foregoing and other features of the present invention will become apparent to those skilled in the art to which the present invention relates upon reading the following description with reference to the accompanying drawings, in which.

DESCRIPTION OF EMBODIMENTS

Figure 1:
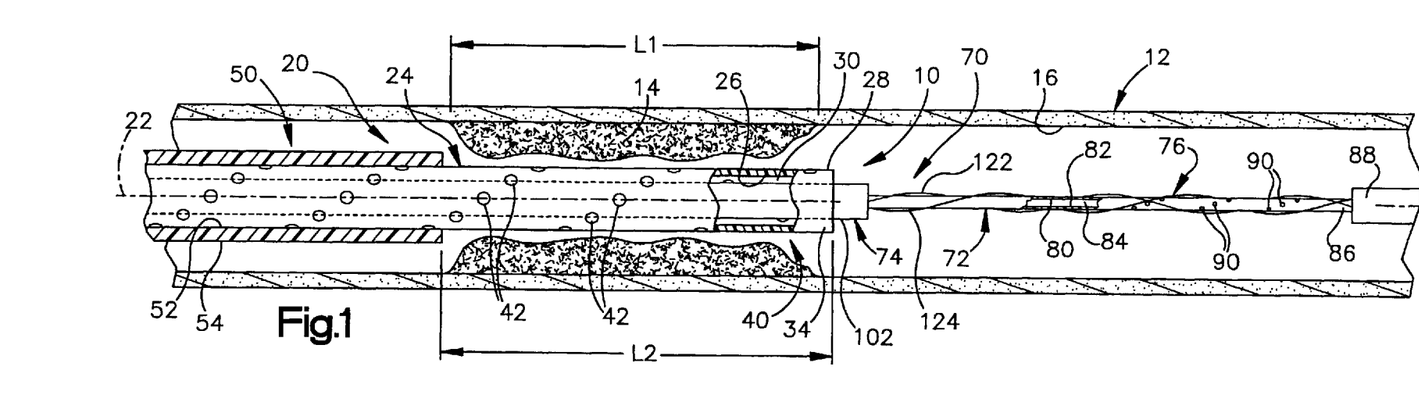
FIG. 1 is a side view, partly in section, of an apparatus for performing thrombolysis constructed in accordance with a first embodiment of the present invention, the apparatus being shown in a first condition.

The present invention relates to an apparatus and method for performing thrombolysis and, more particularly, is directed to an apparatus and method for delivering an infusate into a body lumen to dissolve thrombus. In accordance with a first embodiment of the present invention, FIGS. 1–7 illustrate an apparatus 10 for delivering an infusate into a blood vessel 12 to dissolve thrombus 14 present in the blood vessel. As shown in FIG. 1, the thrombus 14 is adhered to an inner surface 16 of the blood vessel 12 and is undesirably restricting blood flow through the blood vessel. The thrombus 14 extends along the inner surface 16 of the blood vessel 12 over an axial length L1.

The apparatus 10 comprises first and second catheter assemblies 20 and 70 that extend coaxially along an axis 22. The first catheter assembly 20 includes a first catheter 24 and a sheath 50. The first catheter 24 is a tubular member having inner and outer surfaces 26 and 28. In accordance with one embodiment of the invention, the outer surface 28 of the first catheter 24 has an outer diameter, defined by the outer surface, of 0.065 inches (5 French).

The inner surface 26 defines a first lumen 30 that extends through the first catheter 24. An end wall 32 (FIG. 3) extends between the inner and outer surfaces 26 and 28 at a distal end 34 of the first catheter 24. The end wall 32 includes an opening 36 through which the second catheter assembly 70 projects. The end wall 32 seals around the second catheter assembly 70 to minimize fluid leakage through the opening 36.

The first catheter 24 has an infusion section 40 (FIG. 1) that includes a plurality of infusion ports 42 for delivering an infusate, such as a known thrombolytic fluid or agent. In accordance with one feature of the invention, the infusion section 40 has an axial length L2 of up to 50 cm, as measured from the distal end 34 of the first catheter 24. The infusion ports 42 extend from the first lumen 30 through the outer surface 28 and are spaced axially apart. In accordance with the illustrated embodiment, the infusion ports 42 extend along the infusion section 40 in a helical pattern, but could alternatively extend in another suitable pattern. Preferably, the infusion ports 42 vary in size and increase in diameter toward the distal end 34 of the first catheter 24. Having the infusion ports 42 increase in size from the proximal end toward the distal end 34 may provide a more evenly distributed flow pattern throughout the infusion section 40 because the fluid pressure inside the first lumen 30 drops, both from frictional losses and from the thrombolytic fluid escaping through the more proximally located ports, along the axial length L2 toward the distal end. It should, however, be understood that the sizes of the infusion ports could be changed to another suitable configuration. The infusion ports 42 are able to deliver infusate at a flow rate of up to 200 cc/hr.

The sheath 50 coaxially surrounds the first catheter 24 and is axially movable relative to the first catheter. The sheath 50 is a tubular member having inner and outer surfaces 52 and 54. An end wall 56 (FIG. 3) extends between the inner and outer surfaces 52 and 54 at a distal end 58 of the sheath. The end wall 56 includes an opening 60 through which the first catheter 24 projects. The end wall 56 seals around the first catheter 24 to prevent fluid leakage through the opening 60.

In accordance with one embodiment of the invention, the sheath 50 has an outer diameter, defined by the outer surface 54, of no more than 0.078 inches (6 French). The inner surface 52 defines an inner diameter for the sheath 50 that is approximately equal to the outer diameter of the first catheter 24. The close fit between the sheath 50 and the first catheter 24 permits relative movement but prevents fluid from exiting through any of the plurality of infusion ports 42 that are covered over by the sheath.

As described further below, axial movement of the sheath 50 relative to the first catheter 24 enables the surgeon to selectively cover (or uncover) a portion of the plurality of infusion ports 42 in order to control the amount and distribution of infusate delivered by the infusion section 40 of the first catheter. Such movement of the sheath 50 thus varies the axial length L2 of the infusion section 40, which is defined by the uncovered portion of the infusion ports 42. In the illustrated embodiment, the axial length L2 of the infusion section 40 can be varied from 0 to 50 cm. As may be seen by comparing FIGS. 2 and 4, the axial length L2 of the infusion section can be varied according to the size (axial length L1) of the thrombus 14. Further, the sheath 50 is movable, and thus axial length L2 of the infusion section 40 is variable, while infusate is being delivered through the infusion ports 42.

Figure 5:
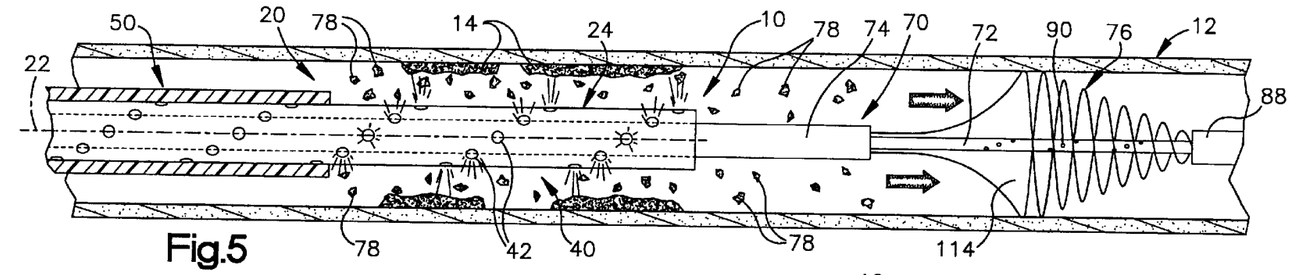
FIGS. 5–7 are side views illustrating the apparatus of FIGS. 1–3 at different stages of the thrombolysis.

The second catheter assembly 70 includes a second catheter 72, a sleeve 74, and a radially expandable filter 76 for trapping dislodged thrombotic material 78 (FIG. 5). The second catheter 72 is a tubular member having inner and outer surfaces 80 and 82 (FIG. 1). The inner surface 80 defines a second lumen 84 that extends through the second catheter 72. The second lumen 84 terminates at a distal end 86 of the second catheter 72. A flexible tip 88 extends from the distal end 86 of the second catheter 72.

The second catheter 72 includes a plurality of infusion ports 90 for delivering an infusate, such as a known thrombolytic fluid or agent. The infusion ports 90 extend from the second lumen 84 through the outer surface 82 and are spaced axially apart. In accordance with the illustrated embodiment, the infusion ports 90 extend along the second catheter 72 in a helical pattern, but could alternatively extend in another suitable pattern. Preferably, the infusion ports 90 vary in size and increase in diameter toward the distal end 86 of the second catheter 72, although it should be understood that the sizes of the infusion ports could be changed to another suitable configuration. The infusion ports 90 are able to deliver infusate at a flow rate of up to 60 cc/hr.

Figure 2:
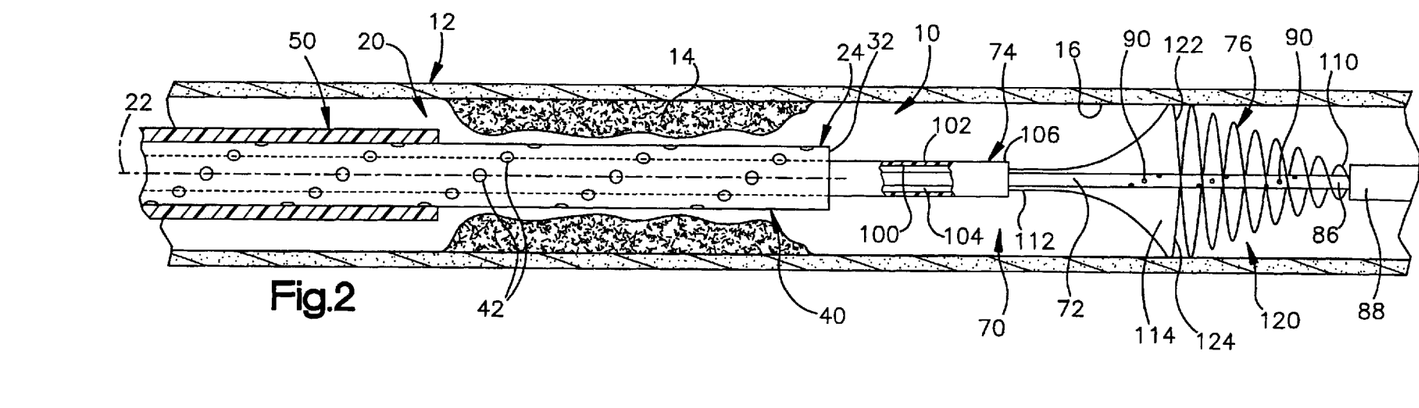
FIG. 2 is a side view showing the apparatus of FIG. 1 in a second condition.

The sleeve 74 coaxially surrounds the second catheter 72 and is axially movable relative to the second catheter. The sleeve 74 is a tubular member having inner and outer surfaces 100 and 102 (FIG. 2). The outer surface 102 is slidably received in the opening 36 through the end wall 32 of the first catheter 24. The inner surface 100 defines a passage 104 inside the sleeve 74 that extends to a distal end 106 of the sleeve.

The filter 76 is radially expandable and is disposed about the second catheter 72. The filter 76 has oppositely disposed first and second ends 110 and 112. The first end 110 of the filter 76 is attached to the distal end 86 of the second catheter in a manner not shown. The second end 112 of the filter 76 is attached to the distal end 106 of the sleeve 74 in a manner not shown. The filter 76 has a collapsed condition, illustrated in FIG. 1, and an expanded condition, illustrated in FIG. 2, in which the filter stretches radially across the blood vessel 12 to form a filter basket 120. The filter 76 is expanded to the condition of FIG. 2 by moving the sleeve 74 distally. In the expanded condition, the filter 76 has an inlet 114. The infusion ports 90 in the second catheter 72 are located within the axial length of the filter basket 120, including the inlet 114.

According to the first embodiment of the invention, the filter 76 comprises a pair of coil members 122 and 124 that, in the expanded condition, have a generally conical shape. The conical shape of the coil members 122 and 124 decreases in size toward the first end 110 of the filter 76. As may be seen in FIGS. 2 and 3, the coil members 122 and 124 are 180° out of phase. It should be apparent to those of ordinary skill in the art that the porosity of the filter 76 can be adjusted by changing the numbers of turns in the coil members 122 and 124.

Figure 3:
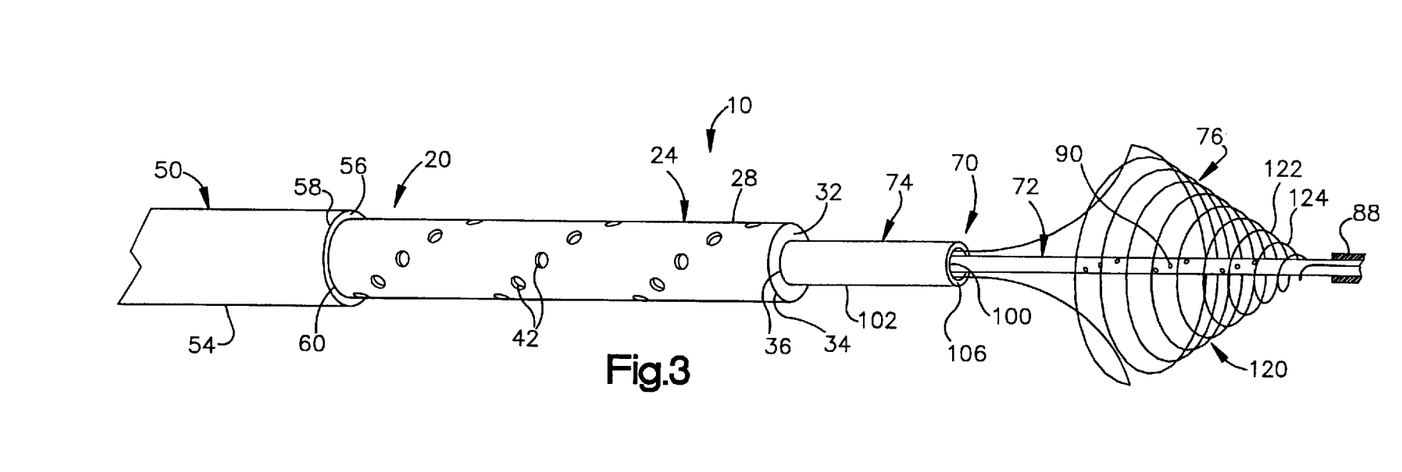
FIG. 3 is a perspective view of the apparatus of FIG. 1.
Figure 4:
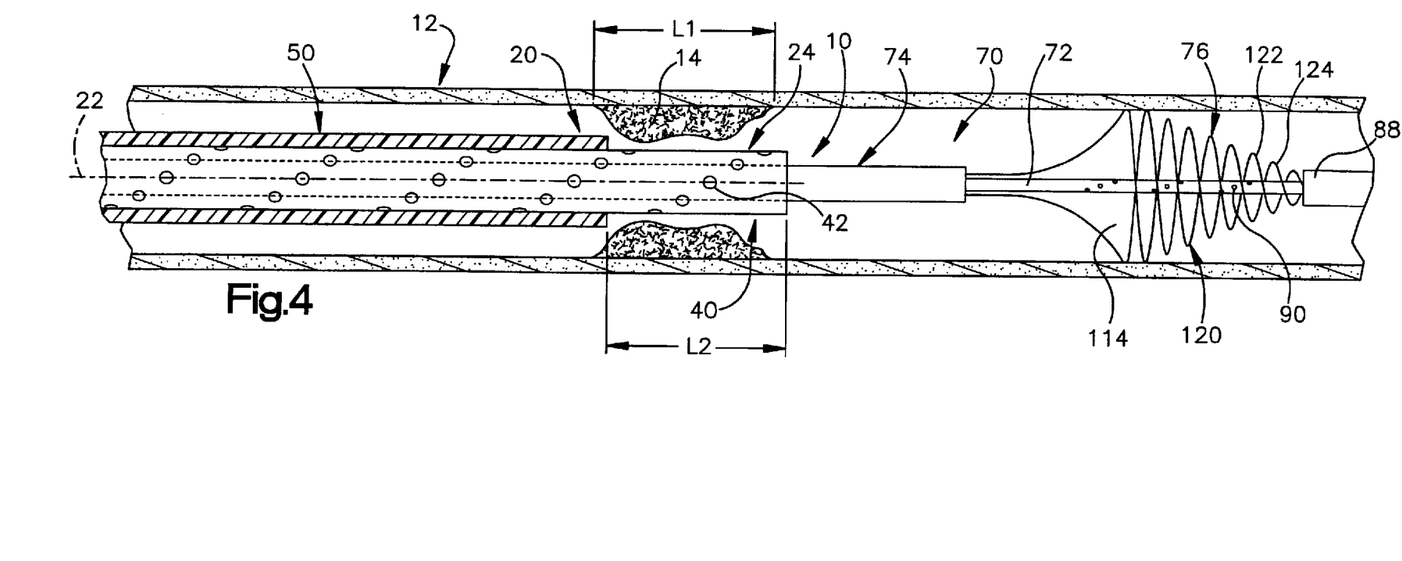
FIG. 4 is a side view illustrating parts of the apparatus of FIG. 2 in different positions.

The coil members 122 and 124 are made of a flexible solid elastic or superelastic material. One such material that is suitable for the coil members 122 and 124 is Nitinol wire, which can be preformed into a memorized shape and subsequently deformed into another shape. In the present invention, the coiled, conical configuration of the coil members 122 and 124 in the expanded condition of FIG. 3 is the memorized shape. The superelastic properties of the material of the coil members 122 and 124 permit the coil members to be straightened to the collapsed condition of FIG. 1 with minimal force and without damage to the coil members.

It should be understood that the coil members 122 and 124 could also be made from a shape memory Nitinol material, which can resume a memorized shape upon heating of the material. The heating of the Nitinol material can be done using electric current or other means, or through normal body heat.

Prior to using the apparatus 10 to perform thrombolysis, the surgeon may elect to determine to the size of the thrombus 14 in the blood vessel 12 using known imaging techniques. Doing so allows the surgeon to set the axial length L2 of the infusion section 40 of the first catheter 24, by moving the sheath 50 relative to the first catheter to uncover a portion of the infusion ports 42, to an optimal initial position.

The first and second catheter assemblies 20 and 70 of the apparatus are then inserted into the blood vessel 12 in a known manner. According to one exemplary manner, a guide wire (not shown) is advanced into the blood vessel 12 to the location of the thrombus 14. The first catheter assembly 20 is then advanced over the guide wire to the position of FIG. 1 in which the infusion section 40, as defined by the uncovered portion of the infusion ports 42, lies adjacent the thrombus 14. The guide wire is then removed and the second catheter assembly 70 is advanced distally through the first catheter assembly 20 to the position illustrated in FIGS. 1 and 2.

The filter 76 is then radially expanded to extend across the blood vessel 14 as shown in FIG. 2. The filter 76 is expanded by moving the sleeve 74 distally from the position shown in FIG. 1 to the position shown in FIG. 2. Upon movement of the sleeve 74, the coil members 122 and 124 that form the filter 76 return to their memorized conical shape. The expanded filter 76 lies approximately 5–10 cm downstream from the distal end 34 of the first catheter 24.

Next, a thrombolytic fluid is infused through the first catheter 24 and directed, through the infusion ports 42 in the infusion section 40, against the thrombus 14 in the blood vessel 14. As may be seen in FIG. 5, the uncovered infusion ports 42 that define the infusion section 40 function as nozzles to direct the thrombolytic fluid radially outward against the thrombus 14. The force of the thrombolytic fluid flow in combination with the chemically active ingredients in the thrombolytic fluid cause the thrombus 14 to dislodge from the inner surface 16 of the blood vessel 12, as shown in FIG. 5, and break into fragments of dislodged thrombotic material 78. Further, the thrombolytic fluid, which is formulated to breakdown the thrombotic material 78, causes the thrombotic material to begin dissolving. As illustrated in FIG. 5, the flow of blood through the blood vessel 12 carries the dislodged thrombotic material 78 distally toward the filter 76.

Figure 6:
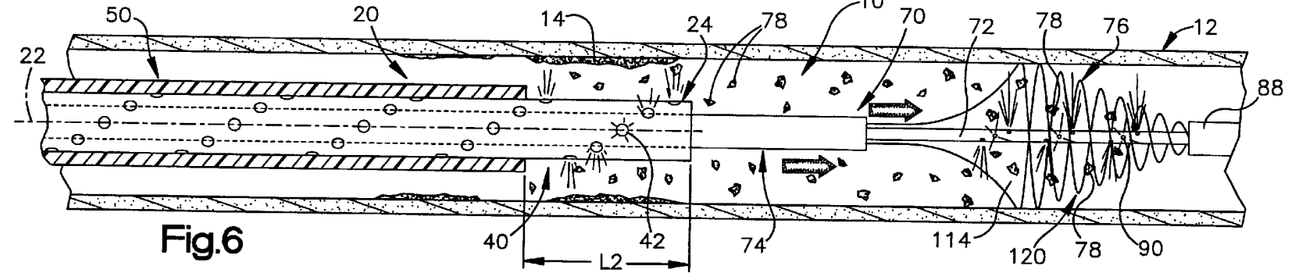

The blood flow carries the fragments of the dislodged thrombotic material 78 through the inlet 114 of the filter and into the filter basket 120 where the fragments become trapped. At or about this time, a thrombolytic fluid is infused through the second catheter 72 and directed, through the infusion ports 90 in the filter basket 120, against the fragments of the thrombotic material 78 trapped in the filter basket 120 as shown in FIG. 6. The thrombolytic fluid infused through the second catheter 72 may be the same thrombolytic fluid as is infused through the first catheter 24, or may be a different thrombolytic fluid. The chemically active ingredients in the thrombolytic fluid infused through the second catheter 72 cause the fragments of the thrombotic material to dissolve in the filter basket 120.

As may be seen in FIG. 6, as the size of the thrombus 14 adhered to the blood vessel 12 decreases, the axial length L2 of the infusion section 40 of the first catheter 24 may be decreased accordingly. Such a change is accomplished by moving the sheath 50 distally to cover over a larger portion of the infusion ports 42, and can be done while the thrombolytic fluid is being infused through the first catheter 24.

Figure 7:
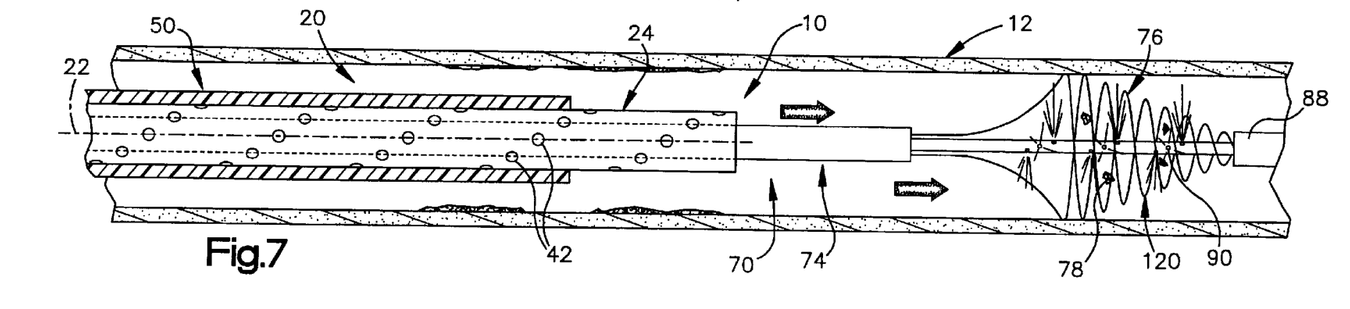

FIG. 7 illustrates that after most, if not all, of the thrombus 14 is dislodged from the inner surface 16 of the blood vessel 12, the flow of thrombolytic fluid through the first catheter 24 is terminated. Meanwhile, the thrombolytic fluid continues to be infused through the infusion ports 90 in the filter 76 to finish dissolving the thrombotic material 78 trapped in the filter basket 120. The flow of thrombolytic fluid infused through the second catheter 72 is terminated when it is believed that most, if not all, of the fragments of thrombotic material 78 trapped in the filter basket 120 have been completely dissolved.

Having completed the thrombolysis, the apparatus 10 is then removed from the blood vessel 12 by reversing the steps used to deploy the apparatus. The sleeve 74 is moved proximally, causing the filter 76 to collapse back to the position of FIG. 1. Any leftover fragments of thrombotic material 78 caught in the filter basket 120 will remain trapped in the collapsed filter 76. Next, the second catheter assembly 70 is retracted into the first catheter assembly 20. The apparatus 10 is then pulled out of the blood vessel 12.

Figure 8:
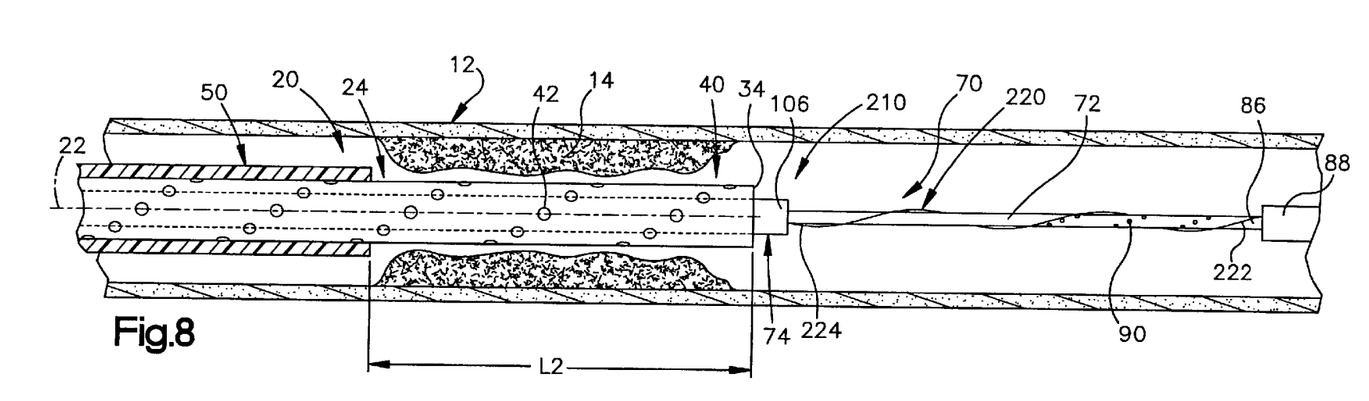
FIG. 8 is a side view, partly in section, of an apparatus for performing thrombolysis constructed in accordance with a second embodiment of the present invention, the apparatus being shown in a first condition.
Figure 9:
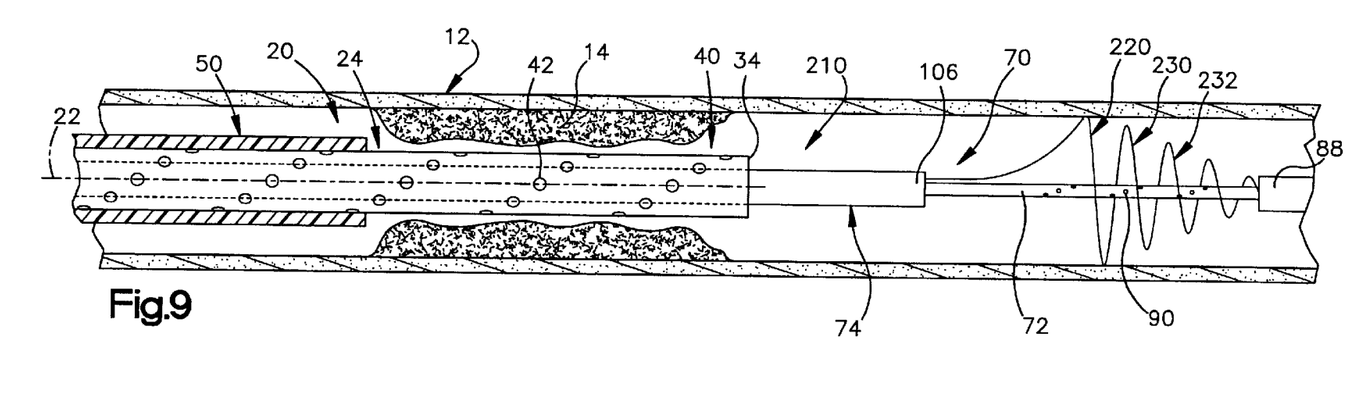
FIG. 9 is a side view showing the apparatus of FIG. 8 in a second condition.

FIGS. 8 and 9 illustrate an apparatus 210 for performing thrombolysis in accordance with a second embodiment of the present invention. In the second embodiment of FIGS. 8 and 9, reference numbers that are the same as those used in the first embodiment of FIGS. 1–7 designate components that are the same as components in the first embodiment.

According to the second embodiment, the apparatus 210 includes a radially expandable filter 220. The filter 220 has oppositely disposed first and second ends 222 and 224. The first end 222 of the filter 220 is attached to the distal end 86 of the second catheter 72. The second end 224 of the filter 220 is attached to the distal end 106 of the sleeve 74. The filter 220 has a collapsed condition, illustrated in FIG. 8, and an expanded condition, illustrated in FIG. 9, in which the filter stretches radially across the blood vessel 12 to form a filter basket 230. The infusion ports 90 in the second catheter 72 are located within the filter basket 230. As in the first embodiment of FIGS. 1–7, the filter 220 is expanded to the condition of FIG. 9 by moving the sleeve 74 distally.

The filter 220 according to the second embodiment comprises a single coil member 232 disposed about the second catheter 72. Similar to the first embodiment, the coil member 232 of the filter 220, in the expanded condition, has a generally conical shape. The conical shape of the coil member decreases 232 in size toward the first end 222 of the filter. It should be apparent to those of ordinary skill in the art that the porosity of the filter 220 can be adjusted by changing the numbers of turns in the coil member 232.

The coil member 232 is made of a flexible solid elastic or superelastic material. One such material that is suitable for the coil member 232 is Nitinol wire, which can be preformed into a memorized shape and subsequently deformed into another shape. In the present invention, the coiled, conical configuration of the coil member 232 in the expanded condition of FIG. 9 is the memorized shape. The superelastic properties of the material of the coil member permits the coil member 232 to be straightened to the collapsed condition of FIG. 8 with minimal force and without damage to the coil member.

It should be understood that the coil member 232 could also be made from a shape memory Nitinol material, which can resume a memorized shape upon heating of the material. The heating of the Nitinol material can be done using electric current or other means, or through normal body heat.

Thrombolysis is performed with the apparatus 210 using the same process as described previously with regard to the apparatus 10 of the first embodiment. The axial length L2 of the infusion section 40 of the first catheter 24 is pre-set, by moving the sheath 50 relative to the first catheter to uncover a portion of the infusion ports 42, to an optimal initial position. The first and second catheter assemblies 20 and 70 of the apparatus 210 are then inserted into the blood vessel 12 and into the position of FIG. 8 in which the infusion section 40, as defined by the uncovered portion of the infusion ports 42, lies adjacent the thrombus 14. When the infusion section 40 reaches the desired position in the blood vessel 12, the second catheter assembly 70 is advanced distally relative to the first catheter assembly 20 to move the second catheter 72 to the position of FIGS. 8 and 9.

The filter 220 is then radially expanded to extend across the blood vessel 12 as shown in FIG. 9. The filter 220 is expanded by moving the sleeve 74 distally from the position shown in FIG. 8 to the position shown in FIG. 9. Upon movement of the sleeve 74, the coil member 232 that forms the filter 220 returns to its memorized conical shape. The expanded filter 220 lies approximately 5–10 cm downstream from the distal end 34 of the first catheter 24.

As described above with regard to the first embodiment and illustrated in FIGS. 5–7, thrombolytic fluids are infused through the infusion ports 42 and 90 in the first and second catheters 24 and 72, respectively, to dislodge the thrombus 14 and dissolve the dislodged thrombotic material 78. The thrombolytic fluid infused through the infusion ports 90 in the second catheter 72 causes the fragments of thrombotic material 78 to dissolve in the filter basket 230. After most, if not all, of the thrombus 14 is dislodged from the inner surface 16 of the blood vessel 12, the flow of thrombolytic fluid through the first catheter 24 is terminated. The flow of thrombolytic fluid infused through the second catheter 72 is terminated when it is believed that most, if not all, of the fragments of thrombotic material 78 trapped in the filter basket 230 have been completely dissolved. Having completed the thrombolysis, the apparatus 210 is then removed from the blood vessel 12 by reversing the steps used to deploy the apparatus.

Figure 10:
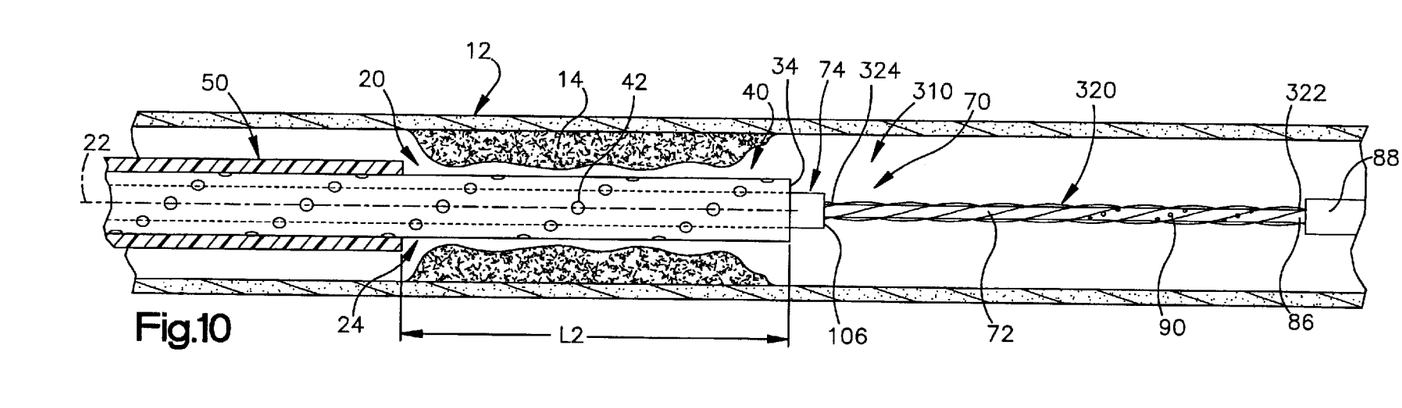
FIG. 10 is a side view, partly in section, of an apparatus for performing thrombolysis constructed in accordance with a third embodiment of the present invention, the apparatus being shown in a first condition.
Figure 11:
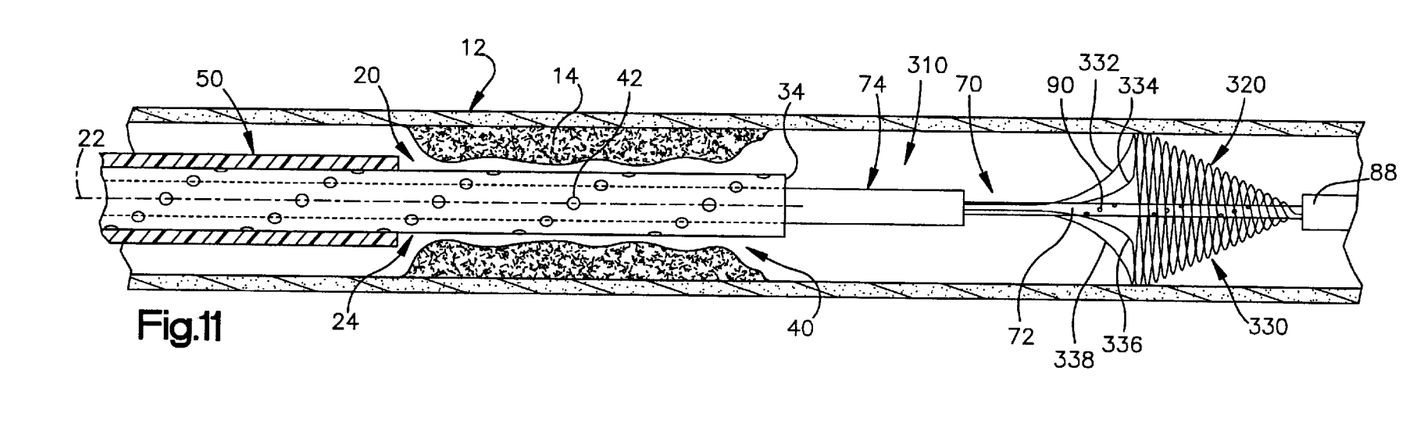
FIG. 11 is a side view showing the apparatus of FIG. 10 in a second condition.

FIGS. 10 and 11 illustrate an apparatus 310 for performing thrombolysis in accordance with a third embodiment of the present invention. In the third embodiment of FIGS. 10 and 11, reference numbers that are the same as those used in the first embodiment of FIGS. 1–7 designate components that are the same as components in the first embodiment.

According to the third embodiment, the apparatus 310 includes a radially expandable filter 320. The filter 320 has oppositely disposed first and second ends 322 and 324. The first end 322 of the filter 320 is attached to the distal end 86 of the second catheter 72. The second end 324 of the filter 320 is attached to the distal end 106 of the sleeve 74. The filter 320 has a collapsed condition, illustrated in FIG. 10, and an expanded condition, illustrated in FIG. 11, in which the filter stretches radially across the blood vessel to form a filter basket 330. The infusion ports 90 in the second catheter 72 are located within the filter basket 330. As in the first embodiment of FIGS. 1–7, the filter 320 is expanded to the condition of FIG. 11 by moving the sleeve 74 distally.

The filter 320 according to the third embodiment comprises four coil members 332, 334, 336 and 338 disposed about the second catheter 72. The four coil members 332–338 are 90° out of phase. Similar to the first embodiment, the coil members 332–338 of the filter 320, in the expanded condition, have a generally conical shape. The conical shape of the coil members 332–338 decreases in size toward the first end 322 of the filter 320. It should be apparent to those of ordinary skill in the art that the porosity of the filter 320 can be adjusted by changing the numbers of turns in the coil members 332–338.

The coil members 332–338 are made of a flexible solid elastic or superelastic material. One such material that is suitable for the coil members 332–338 is Nitinol wire, which can be preformed into a memorized shape and subsequently deformed into another shape. In the present invention, the coiled, conical configuration of the coil members 332–338 in the expanded condition of FIG. 11 is the memorized shape. The superelastic properties of the material of the coil members 332–338 permits the coil members to be straightened to the collapsed condition of FIG. 10 with minimal force and without damage to the coil members.

It should be understood that the coil members 332–338 could also be made from a shape memory Nitinol material, which can resume a memorized shape upon heating of the material. The heating of the Nitinol material can be done using electric current or other means, or through normal body heat.

Thrombolysis is performed with the apparatus 310 using the same process as described previously with regard to the apparatus 10 of the first embodiment. The axial length L2 of the infusion section 40 of the first catheter 24 is pre-set, by moving the sheath 50 relative to the first catheter to uncover a portion of the infusion ports 42, to an optimal initial position. The first and second catheter assemblies 20 and 70 of the apparatus 310 are then inserted into the blood vessel 12 and into the position of FIG. 10 in which the infusion section 40, as defined by the uncovered portion of the infusion ports 42, lies adjacent the thrombus 14. When the infusion section 40 reaches the desired position in the blood vessel 12, the second catheter assembly 70 is advanced distally relative to the first catheter assembly 20 to move the second catheter 72 to the position of FIGS. 10 and 11.

The filter 320 is then radially expanded to extend across the blood vessel 12 as shown in FIG. 11. The filter 320 is expanded by moving the sleeve 74 distally from the position shown in FIG. 10 to the position shown in FIG. 11. Upon movement of the sleeve 74, the coil members 332–338 that form the filter 320 returns to their memorized conical shape. The expanded filter 320 lies approximately 5–10 cm downstream from the distal end 34 of the first catheter 24.

As described above with regard to the first embodiment and illustrated in FIGS. 5–7, thrombolytic fluids are infused through the infusion ports 42 and 90 in the first and second catheters 24 and 72, respectively, to dislodge the thrombus 14 and dissolve the dislodged thrombotic material 78. The thrombolytic fluid infused through the infusion ports 90 in the second catheter 72 causes the fragments of thrombotic material 78 to dissolve in the filter basket 330. After most, if not all, of the thrombus 14 is dislodged from the inner surface 16 of the blood vessel 12, the flow of thrombolytic fluid through the first catheter 24 is terminated. The flow of thrombolytic fluid infused through the second catheter 72 is terminated when it is believed that most, if not all, of the fragments of thrombotic material 78 trapped in the filter basket 330 have been completely dissolved. Having completed the thrombolysis, the apparatus 310 is then removed from the blood vessel 12 by reversing the steps used to deploy the apparatus.

Figure 12:
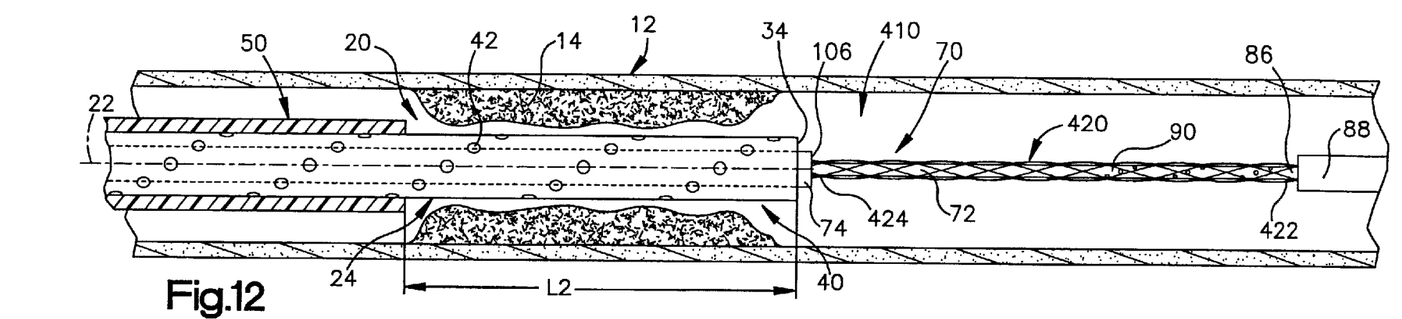
FIG. 12 is a side view, partly in section, of an apparatus for performing thrombolysis constructed in accordance with a fourth embodiment of the present invention, the apparatus being shown in a first condition.
Figure 13:
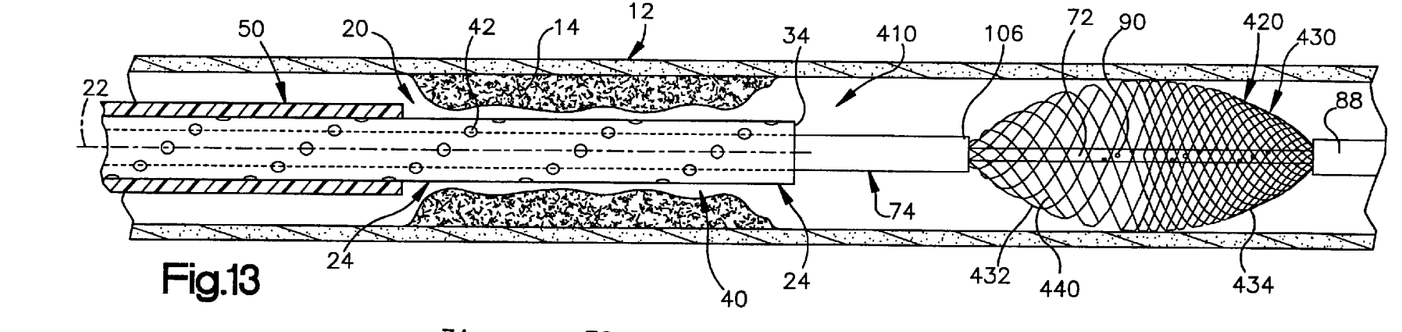
FIG. 13 is a side view showing the apparatus of FIG. 12 in a second condition.
Figure 13A:
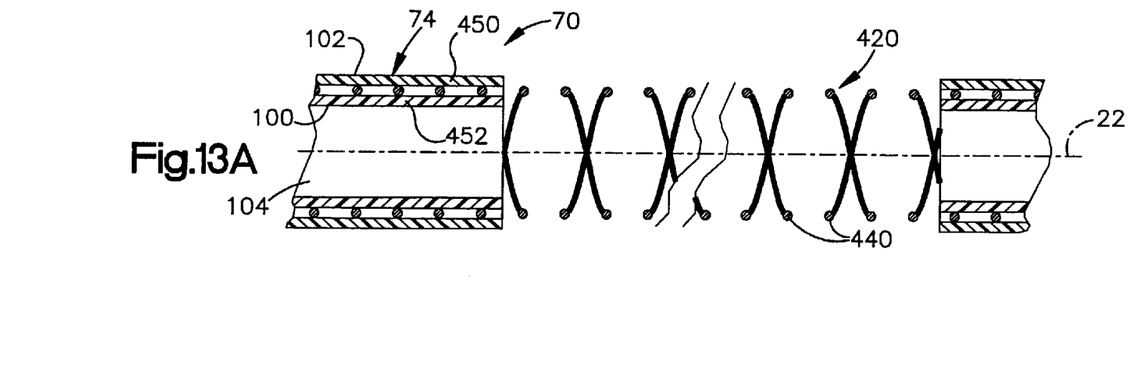
FIG. 13A is an enlarged view of a portion of the apparatus of FIG. 12 in accordance with an alternate construction.

FIGS. 12 and 13 illustrate an apparatus 410 for performing thrombolysis in accordance with a fourth embodiment of the present invention. In the fourth embodiment of FIGS. 12 and 13, reference numbers that are the same as those used in the first embodiment of FIGS. 1–7 designate components that are the same as components in the first embodiment.

According to the fourth embodiment, the apparatus 410 includes a radially expandable filter 420. The filter 420 has oppositely disposed first and second ends 422 and 424. The first end 422 of the filter 420 is attached to the distal end 86 of the second catheter 72. The second end 424 of the filter 420 is attached to the distal end 106 of the sleeve 74. The filter 420 has a collapsed condition, illustrated in FIG. 12, and an expanded condition, illustrated in FIG. 13, in which the filter stretches radially across the blood vessel to form a filter basket 430. The infusion ports 90 in the second catheter 72 are located within the filter basket 430. As in the first embodiment of FIGS. 1–7, the filter 420 is expanded to the condition of FIG. 13 by moving the sleeve 74 distally.

The filter basket 430 according to the fourth embodiment has a proximal half 432 with a relatively loose mesh to allow blood carrying dislodged thrombotic material 78 to enter the filter 420. The filter basket 430 has a distal half 434 with a relatively tight mesh to trap the dislodged thrombotic material 78 as blood flows through the filter 420.

The filter basket 430 is made of wires 440 or filaments, and may be braided, knitted or woven. According to one manufacturing method, the filter basket 430 comprises forty wires 440 that are braided into ten wire bundles to form the relatively loose mesh of the proximal half 432 of the filter basket. The forty wires 440 remain unbraided (extend individually) to form the relatively tight mesh in the distal half 434 of the filter basket 430.

It is contemplated that the second catheter assembly 70 could also be made using a three layer construction to form the sleeve 74 and the filter 420. As may be seen in FIG. 18, the sleeve 74 comprises an outer layer 450, an inner layer 452, and the braided wires 440 that form the filter 420. The outer and inner layers 450 and 452 may be made of nylon or polyurethane that is heat-fused over the wires 440 and is then selectively removed during the manufacture of the sleeve 74 to reveal a desired length of the wires. The outer and inner layers 450 and 452 may be removed chemically, by masking off a portion of the layers and exposing the unmasked portions to a solvent, or through other means such as a laser. As with the previous embodiments, the distal end of the filter 420 is attached to the distal end 86 of the second catheter 72 in a manner not shown.

Thrombolysis is performed with the apparatus 410 using the same process as described previously with regard to the apparatus 10 of the first embodiment. The axial length L2 of the infusion section 40 of the first catheter 24 is pre-set, by moving the sheath relative 50 to the first catheter to uncover a portion of the infusion ports 42, to an optimal initial position. The first and second catheter assemblies 20 and 70 of the apparatus 410 are then inserted into the blood vessel 12 and into the position of FIG. 12 in which the infusion section 40, as defined by the uncovered portion of the infusion ports 42, lies adjacent the thrombus 14. When the infusion section 40 reaches the desired position in the blood vessel 12, the second catheter assembly 70 is advanced distally relative to the first catheter assembly 20 to move the second catheter 72 to the position of FIGS. 12 and 13.

The filter 420 is then radially expanded to extend across the blood vessel 12 as shown in FIG. 13. The filter 420 is expanded by moving the sleeve 74 distally from the position shown in FIG. 12 to the position shown in FIG. 13.

As described above with regard to the first embodiment and illustrated in FIGS. 5–7, thrombolytic fluids are infused through the infusion ports 42 and 90 in the first and second catheters 24 and 72, respectively, to dislodge the thrombus 14 and dissolve the dislodged thrombotic material 78. The thrombolytic fluid infused through the infusion ports 90 in the second catheter 72 causes the fragments of thrombotic material 78 to dissolve in the filter basket 430. After most, if not all, of the thrombus 14 is dislodged from the inner surface 16 of the blood vessel 12, the flow of thrombolytic fluid through the first catheter 24 is terminated. The flow of thrombolytic fluid infused through the second catheter 72 is terminated when it is believed that most, if not all, of the fragments of thrombotic material 78 trapped in the filter basket 430 have been completely dissolved. Having completed the thrombolysis, the apparatus 410 is then removed from the blood vessel 12 by reversing the steps used to deploy the apparatus.

Figure 14:
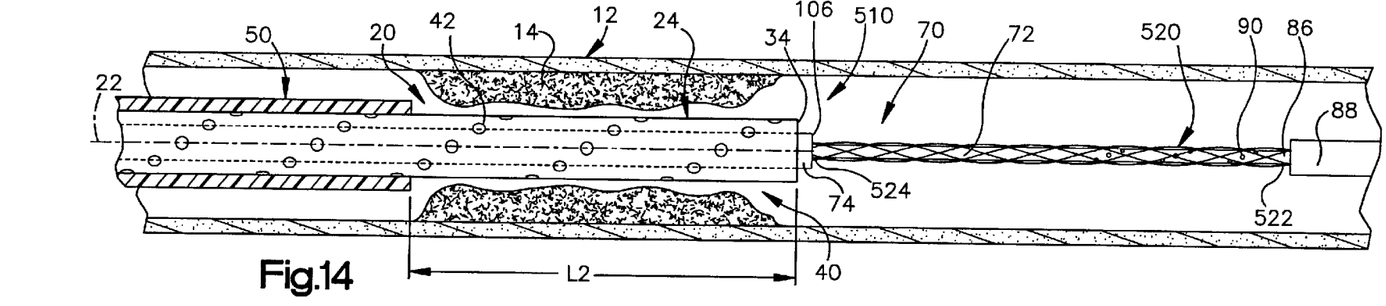
FIG. 14 is a side view, partly in section, of an apparatus for performing thrombolysis constructed in accordance with a fifth embodiment of the present invention, the apparatus being shown in a first condition.
Figure 15:
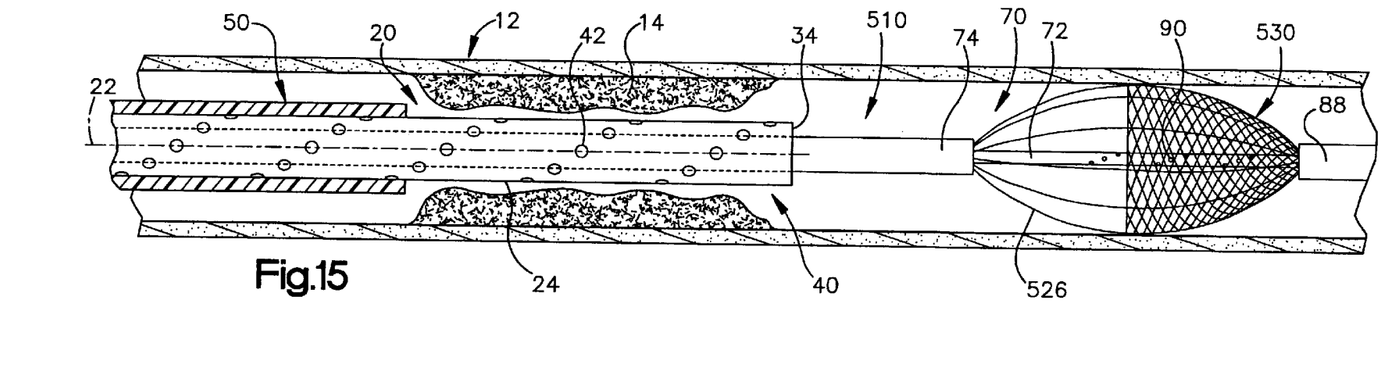
FIG. 15 is a side view showing the apparatus of FIG. 14 in a second condition.

FIGS. 14 and 15 illustrate an apparatus 510 for performing thrombolysis in accordance with a fifth embodiment of the present invention. In the fifth embodiment of FIGS. 14 and 15, reference numbers that are the same as those used in the first embodiment of FIGS. 1–7 designate components that are the same as components in the first embodiment.

According to the fifth embodiment, the apparatus 510 includes a radially expandable filter 520. The filter 520 has oppositely disposed first and second ends 522 and 524. The first end 522 of the filter 520 is attached to the distal end 86 of the second catheter 72. The second end 524 of the filter 520 is attached to the distal end 106 of the sleeve 74. The filter 520 has a collapsed condition, illustrated in FIG. 14, and an expanded condition, illustrated in FIG. 15, in which the filter stretches radially across the blood vessel 12 to form a filter basket 530. The infusion ports 90 in the second catheter 72 are located within the filter basket 530. As in the first embodiment of FIGS. 1–7, the filter 520 is expanded to the condition of FIG. 15 by moving the sleeve 74 distally.

The filter 520 according to the fifth embodiment comprises a proximal half 522 and a distal half 524. The proximal half 522 is formed by support wires 526 that are spaced apart so as to allow dislodged thrombotic material 78 to enter the filter 520. The distal half 524 comprises of the filter 520 comprises the filter basket 530 which is supported by the support wires 526 from the proximal half 522. The basket 530 is made of a fabric or polymeric material that has a relatively tight mesh to trap the dislodged thrombotic material 78 as blood flows through the filter 520.

Thrombolysis is performed with the apparatus 510 using the same process as described previously with regard to the apparatus 10 of the first embodiment. The axial length L2 of the infusion section 40 of the first catheter 24 is pre-set, by moving the sheath 50 relative to the first catheter to uncover a portion of the infusion ports 42, to an optimal initial position. The first and second catheter assemblies 20 and 70 of the apparatus 510 are then inserted into the blood vessel and into the position of FIG. 14 in which the infusion section 40, as defined by the uncovered portion of the infusion ports 42, lies adjacent the thrombus 14. When the infusion section 40 reaches the desired position in the blood vessel 12, the second catheter assembly 70 is advanced distally relative to the first catheter assembly 20 to move the second catheter 72 to the position of FIGS. 14 and 15.

The filter 520 is then radially expanded to extend across the blood vessel 12 as shown in FIG. 15. The filter 520 is expanded by moving the sleeve 74 distally from the position shown in FIG. 14 to the position shown in FIG. 15.

As described above with regard to the first embodiment and illustrated in FIGS. 5–7, thrombolytic fluids are infused through the infusion ports 42 and 90 in the first and second catheters 24 and 72, respectively, to dislodge the thrombus 14 and dissolve the dislodged thrombotic material 78. The thrombolytic fluid infused through the infusion ports 90 in the second catheter 72 cause the fragments of the thrombotic material 78 to dissolve in the filter basket 530. After most, if not all, of the thrombus 14 is dislodged from the inner surface 16 of the blood vessel 12, the flow of thrombolytic fluid through the first catheter 24 is terminated. The flow of thrombolytic fluid infused through the second catheter 90 is terminated when it is believed that most, if not all, of the fragments of thrombotic material 78 trapped in the filter basket 530 have been completely dissolved. Having completed the thrombolysis, the apparatus 510 is then removed from the blood vessel 12 by reversing the steps used to deploy the apparatus.

Figure 16:
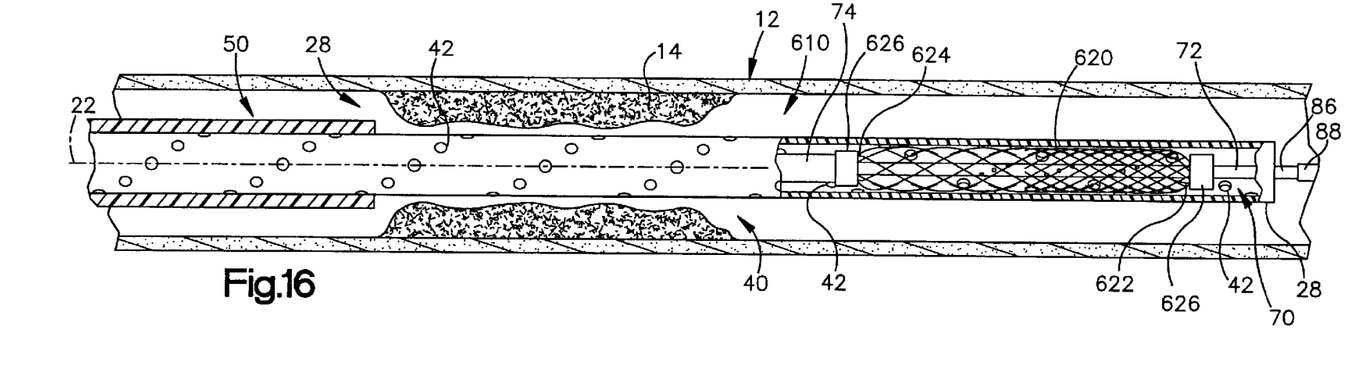
FIG. 16 is a side view, partly in section, of an apparatus for performing thrombolysis constructed in accordance with a sixth embodiment of the present invention, the apparatus being shown in a first condition.
Figure 17:
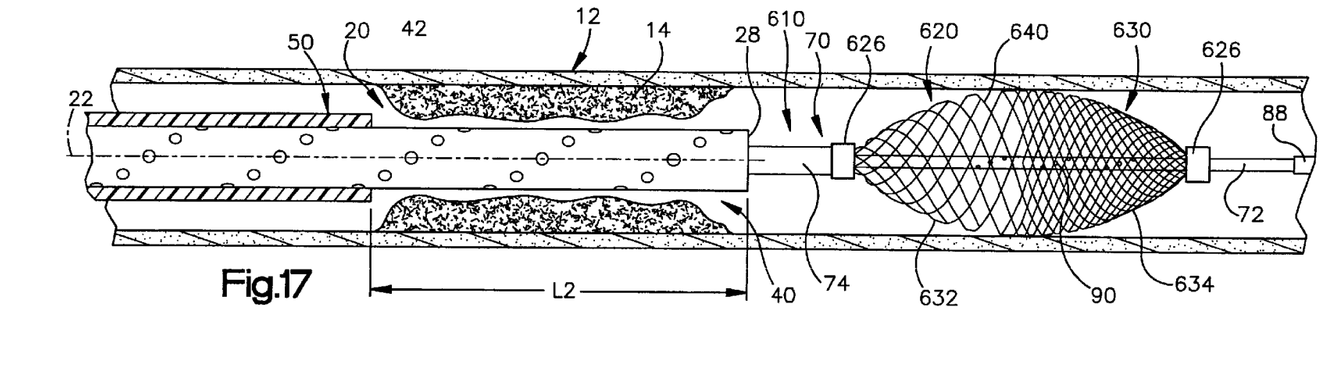
FIG. 17 is a side view showing the apparatus of FIG. 16 in a second condition.

FIGS. 16 and 17 illustrate an apparatus 610 for performing thrombolysis in accordance with a sixth embodiment of the present invention. In the sixth embodiment of FIGS. 16 and 17, reference numbers that are the same as those used in the first embodiment of FIGS. 1–7 designate components that are the same as components in the first embodiment.

According to the sixth embodiment, the apparatus 610 includes a self-expanding filter 620 that does not retract and move inside the sleeve 74 as in the previous embodiments. The sleeve 74 does not move relative to the second catheter 72. The filter 620 has oppositely disposed first and second ends 622 and 624. The first and second ends 622 and 624 of the filter 620 are attached by collars 626, the second catheter 72 and the sleeve 74, respectively. The filter 620 has a collapsed condition (FIG. 16), in which the filter and the second catheter 72 are disposed within the first catheter 24, and an expanded condition (FIG. 17), in which the filter stretches radially across the blood vessel 12 to form a filter basket 630. The infusion ports 90 in the second catheter 72 are located within the filter basket 630. The filter 620 is expanded from the collapsed condition of FIG. 16 to the expanded condition of FIG. 17 by pulling back on the first catheter 24 to release the filter as described further below.

The filter basket 630 according to the sixth embodiment is constructed in a similar manner to the filter basket 430 according to the fourth embodiment of FIGS. 12 and 13. The filter basket 630 has a proximal half 632 with a relatively loose mesh to allow blood carrying dislodged thrombotic material 78 to enter the filter 620. The filter 630 has a distal half 634 with a relatively tight mesh to trap the dislodged thrombotic material 78 as blood flows through the filter 20.

The filter basket 630 is made of braided wires 640. According to one manufacturing method, the filter basket 630 comprises forty wires 640 that are braided into ten wire bundles to form the relatively loose mesh of the proximal half 632 of the filter basket. The forty wires 640 remain unbraided (extend individually) to form the relatively tight mesh in the distal half 634 of the filter basket 630.

The wires 640 of the filter basket 630 are made of a flexible solid elastic or superelastic material. One such material that is suitable for the wires 640 is Nitinol, which can be preformed into a memorized shape and subsequently deformed into another shape. In the present invention, the configuration of the wires 640 in the expanded condition of FIG. 17 is the memorized shape that the wires return to upon being released from inside the first catheter 24.

Thrombolysis is performed with the apparatus 610 using a similar, but not identical, process to that which was described previously with regard to the apparatus 10 of the first embodiment. The first and second catheter assemblies 20 and 70 of the apparatus 610 are inserted into the blood vessel and into a first position shown in FIG. 16. The first position of FIG. 16 places the filter 620 is a desired location downstream of the thrombus 14 for trapping dislodged thrombotic material 78.

Next, the first catheter 24 is pulled backward in the blood vessel 12 and moved relative to the second catheter 72 to release the filter 620 for expansion. The self-expanding filter 620 then expands radially across the blood vessel 12 as shown in FIG. 17. The first catheter 24 is pulled backwards until it reaches a desired position, shown in FIG. 17, in which the infusion section 40 (as defined by the uncovered portion of the infusion ports 42) lies adjacent the thrombus 14.

As described above with regard to the first embodiment and illustrated in FIGS. 5–7, thrombolytic fluids are infused through the infusion ports 42 and 90 in the first and second catheters 20 and 70, respectively, to dislodge the thrombus 14 and dissolve the dislodged thrombotic material 78. The thrombolytic fluid infused through the infusion ports 90 in the second catheter causes the fragments of the thrombotic material 78 to dissolve in the filter basket 630. After most, if not all, of the thrombus 14 is dislodged from the inner surface 16 of the blood vessel 12, the flow of thrombolytic fluid through the first catheter 24 is terminated. The flow of thrombolytic fluid infused through the second catheter 72 is terminated when it is believed that most, if not all, of the fragments of thrombotic material 78 trapped in the filter basket 630 have been completely dissolved. Having completed the thrombolysis, the apparatus 610 is then removed from the blood vessel 12 by reversing the steps used to deploy the apparatus.

Each of the apparatuses disclosed above thus provides an infusion catheter for performing thrombolysis in which the infusion length L2 can be varied, either before or during the thrombolysis procedure, according to the size of the thrombus 14 in a blood vessel 12. Further, each of the apparatuses disclosed above substantially reduces or dissolves, by virtue of the infusion ports 90 located within the filter, the thrombotic material 78 trapped by the filter so that the filter can be easily retracted and removed.

From the above description of the invention, those skilled in the art will perceive improvements, changes and modifications. For example, it should be understand that the apparatuses disclosed above can be used in a wide variety of different blood vessels by altering the dimensions of the apparatuses accordingly. Such improvements, changes and modifications within the skill of the art are intended to be covered by the appended claims.

Having described the invention, we claim:

1. Apparatus for insertion into a blood vessel for eliminating thrombus in the blood vessel, said apparatus comprising:
    a primary thrombolytic fluid delivery system comprising a first group of infusion ports for delivering a first amount of thrombolytic fluid which chemically reacts with an initially whole thrombus structure to cause the thrombus structure to chemically breakdown into several thrombus fragments smaller than the initially whole thrombus structure, and
    a secondary thrombolytic fluid delivery system, located axially spaced apart from the primary thrombolytic fluid delivery system, comprising a filter member for trapping the several thrombus fragments and a second group of infusion ports located in the filter member for delivering a second amount of thrombolytic fluid which chemically reacts with the several thrombus fragments to cause the several thrombus fragments to further chemically breakdown and completely dissolve in the filter member.

2. The apparatus according to claim 1, wherein the primary and secondary thrombolytic fluid delivery systems comprise relatively movable first and second tubular members for insertion into the blood vessel.

3. The apparatus according to claim 1 wherein the primary thrombolytic fluid delivery system comprises the only means for loosening and separating the whole thrombus structure into several thrombus fragments.

4. The apparatus according to claim 1 wherein the filter member is radially expandable to stretch across the blood vessel and trap the several thrombus fragments carried by blood flowing through the blood vessel.

5. The apparatus according to claim 2 wherein the first and second groups of infusion ports are spaced along an infusion section of the respective first and second tubular members in a helical pattern.

6. The apparatus according to claim 1 wherein the first and second groups of infusion ports can deliver the thrombolytc fluid at a rate of up to 60 cc/hr.

7. The apparatus according to claim 2 wherein the first and second groups of infusion ports vary in size and increase in diameter toward a distal end of the first and second tubular members.

8. The apparatus according to claim 1 wherein the filter member comprises a mesh basket having a proximal end that has a relatively loose mesh to allow blood carrying the dislodged thrombus to enter the filter member and a distal end that has a relatively tight mesh to trap the several thrombus fragments as the blood flows through the filter member.

9. The apparatus according to claim 1 wherein the filter member has a distal end comprising a basket and a proximal end comprising support wires for supporting the basket.

10. The apparatus according to claim 1 wherein the filter member comprises at least one coil member that, when expanded, has a generally conical shape.

11. A method for intravascularly eliminating thrombus attached to a wall of a blood vessel, the method comprising the steps of:
    inserting a primary and a secondary thrombolytic fluid delivery system into the blood vessel, the secondary thrombolytic fluid delivery system including a filter basket located downstream from the thrombus and downstream from the primary thrombolytic fluid delivery system;
    delivering a first amount of thrombolytic fluid from the primary thrombolytic fluid delivery system to cause the thrombus structure to chemically breakdown into several thrombus fragments smaller than the initially whole thrombus structure;
    trapping the several thrombus fragments in the filter basket;
    delivering a second amount of thrombolytic fluid from the secondary thrombolytic fluid delivery system to cause the several thrombus fragments to further chemically breakdown and completely dissolve in the filter basket;
    collapsing the filter basket; and
    retracting the primary and secondary thrombolytic fluid delivery systems from the blood vessel without substantially any thrombus remaining within the filter basket.

* * * * *